United States Patent [19]

Quinn

[11] Patent Number: 5,419,195
[45] Date of Patent: May 30, 1995

[54] ULTRASONIC BOOTED HEAD PROBE FOR MOTOR BORE INSPECTION

[75] Inventor: James R. Quinn, Pleasanton, Calif.

[73] Assignee: Westinghouse Electric Corporation, Pittsburgh, Pa.

[21] Appl. No.: 54,182

[22] Filed: Apr. 30, 1993

[51] Int. Cl.⁶ .................. G01N 29/10; G01N 29/28
[52] U.S. Cl. ............................. 73/623; 73/644
[58] Field of Search ............ 73/620, 622, 623, 625, 73/628, 633, 644

[56] References Cited

U.S. PATENT DOCUMENTS

| | | | |
|---|---|---|---|
| 2,992,553 | 7/1961 | Joy | 73/644 |
| 3,921,440 | 11/1975 | Toth | 73/622 |
| 3,952,581 | 4/1976 | Gottelt | 73/67.8 S |
| 4,030,370 | 6/1977 | Keith, Jr. | 73/67.8 S |
| 4,162,636 | 7/1979 | Lather et al. | 73/638 |
| 4,304,134 | 12/1981 | Rouse et al. | 73/634 |
| 4,306,459 | 12/1981 | Johnson et al. | 73/623 |
| 4,576,034 | 3/1986 | Ferree et al. | 73/1 DV |
| 4,586,380 | 5/1986 | Patterson | 73/623 |
| 4,757,716 | 7/1988 | Nottingham et al. | 73/623 |

FOREIGN PATENT DOCUMENTS

| | | |
|---|---|---|
| 58-137750 | 8/1983 | Japan . |
| 59-116539 | 7/1984 | Japan . |

*Primary Examiner*—Hezron E. Williams
*Assistant Examiner*—Rose M. Finley

[57] ABSTRACT

An ultrasonic probe is housed in a probe housing filled with fluid under controlled pressure. The probe provides ultrasonic sound through the fluid to a bladder which presses against the interior of a rotor wall. Located along the periphery of the bladder, a fluid wiper/soaker conduit provides droplets of fluid to the wall of the rotor bore to minimize friction between the bladder and the rotor bore wall and provide an ultrasonic path between the bladder and the rotor wall.

8 Claims, 2 Drawing Sheets

ULTRASONIC BOOTED HEAD PROBE FOR MOTOR BORE INSPECTION

TECHNICAL FIELD

This invention relates generally to techniques for inspecting rotor bores and, in particular, the use of a ultrasonic booted-head probe for rotor bore inspection.

BACKGROUND OF THE INVENTION

For many years, there has been increasing interest and a growing demand for equipment and methods that can be used to inspect power generation turbine and generator rotors for material discontinuities and degradation, which can lead to premature and possible catastrophic rotor failure. Through the use of these inspection techniques, rotor life can be extended. The center portion of the steel forging, from which the rotors are made, are the regions most susceptible to rotor discontinuity and other forms of material degradation. In fact, one reason that a central bore hole is machined in most rotors is to provide the capability to remove suspicious material. Moreover, the operating conditions in the region of the central bore holes in these rotors can produce thermal creep, fatigue and thermal embrittlement, particularly, if there are forging discontinuities. It is with these problems in mind that there is a great interest in developing techniques for enabling accurate rotor inspection, especially techniques using non-destructive inspection methods.

Ultrasonic inspection within the bore is a process that has been used since the early to mid-1980's with fairly wide acceptance as a practical high volume inspection technique. Ultrasonic inspection, also known as boresonic inspection, uses ultrasonic transducers that are transported through the central bore hole by a convenient method. The transducers generate ultrasonic beams that are directed from the bore surface into the rotor material, producing an ultra sonic wave that penetrates the rotor material. By collecting, processing and observing the reflective characteristics of the wave within the forging, the integrity of the material can be deduced. An entire rotor is inspected by placing the transducers around the rotor circumference and along the length of the bore and directing the ultrasonic beam into the material.

Some traditional methods of ultrasonic rotor bore inspection employ a "contact" probe, which nothing more than a transducer housed on a rigid shoe that slides along the bore surface on a layer of oil. The profile of the shoe is matched to the bore curvature. Though this inspection technique has been widely accepted as a near industry standard, it presents some serious drawbacks. The "contact probe" provides low resolution and sensitivity mainly because the contact shoe has a fixed curvature. Different shoes are therefore required for different bore curvatures, increasing the complexity and cost of the equipment and the time required to perform tests, taking into account the fact that the shoes need to be changed for different rotor shapes.

A second method of ultrasonic rotor bore inspection uses an immersion focus probe. All the transducers are placed within the rotor bore and the bore is then filled with oil. The transducers are moved freely through the oil, with the probe focusing on the bore hole to provide a high resolution and sensitivity reflective signals. The problem with this approach is that it calls for flooding the bore removal of air bubbles and proper positioning of the transducers and sealing the bore once filled with oil. The equipment for this is not portable except perhaps on a truck. In addition, the technique is time consuming and complex, and consequently expensive.

DISCLOSURE OF THE INVENTION

Among the objects of the present invention is to provide an improved technique for ultrasonic inspection of rotor bores.

According to the invention, transducers are contained inside of a transducer housing which is extended radially and longitudinally within the bore. The housing is filled with oil under pressure, and, at one end, contains a flexible bladder through which the ultrasonic signals from the transducers are transmitted to the interior wall of the rotor bore, on which the bladder rests when the bore is tested. The interior wall of the rotor bore is covered with an oil film.

According to one aspect of the invention, oil is applied to the area between the bladder and the rotor bore from an oil dispenser around the bladder.

Among the features of the present invention, it provides an inexpensive and precise technique for performing ultrasonic inspection longitudinally and radially in the interior of a rotor bore. A particular feature of the present invention is that the boot bladder, being flexible, conforms to the inner surface of the rotor bore. As a consequence, one probe embodying the present invention can be used to inspect bores with a wide variety of different diameters.

Other objects, benefits and features of the invention will be apparent to one skilled in the art from the following discussion.

BEST MODE FOR CARRYING OUT THE INVENTION

Figure 1:
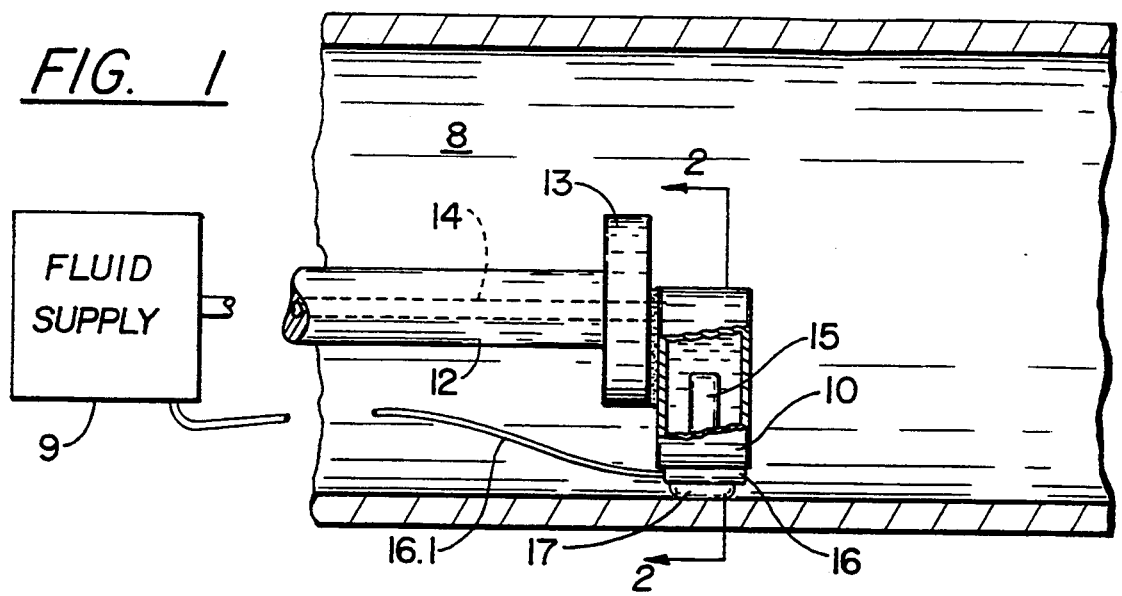
FIG. 1 is a cut-away view of a rotor bore containing a probe that embodies the present invention.
Figure 2:
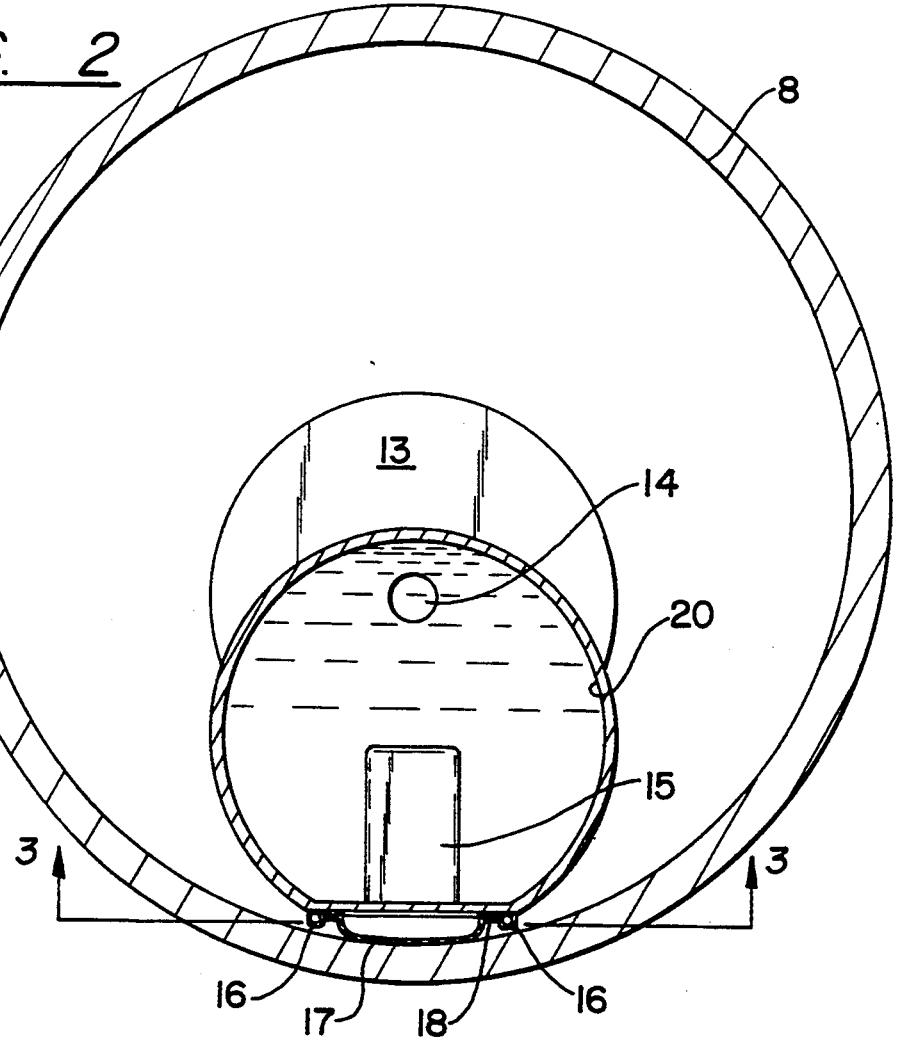
FIG. 2 is a cut-away view from direction two in FIG. 1.

Referring to FIG. 1, a rotor 8 is shown cut-away to expose a system embodying the present invention. The system includes a transducer probe 10 that is attached to a generally circular flange 13, which is part of an extension rod 12. The extension rod 12 contains a bore 14 by which fluid, such as oil, is injected into the interior of the probe 10 under pressure. The probe 10, which is shown partially cut-away contains a transducer assembly 15. The transducer assembly is assumed to comprise a plurality of ultrasonic transducers of the type used in the prior art in ultrasonic inspection. One transducer can be used, but with a commensurate change in test accuracy. The fluid is also applied under pressure to a lubricating ring (wiper) 16. A fluid line 16.1 supplies the fluid to the ring. The transducer assembly 15 should be understood to be capable of transceiver operation by generating ultrasonic waves in response to electrical signals from a control systems (not shown) and receiving the ultrasonic signals reflected back from a surface to produce electrical signals that are supplied to the control system, where the signals are processed to determine differences between the generated and received waves. At the bottom of the probe is a bladder 17 which presses on the inner wall of the rotor 8, conforming to its shape, being flexible. Fluid from the probe 10 separates the bladder from the output of the probe assembly. Though not shown in detail here for convenience and because it is widely discussed in prior art, the probe 15 is assumed to produce output signals that can be processed or interpreted using known signal processing techniques to determine discontinuities and irregularities in the rotor wall 8.

Figure 3:
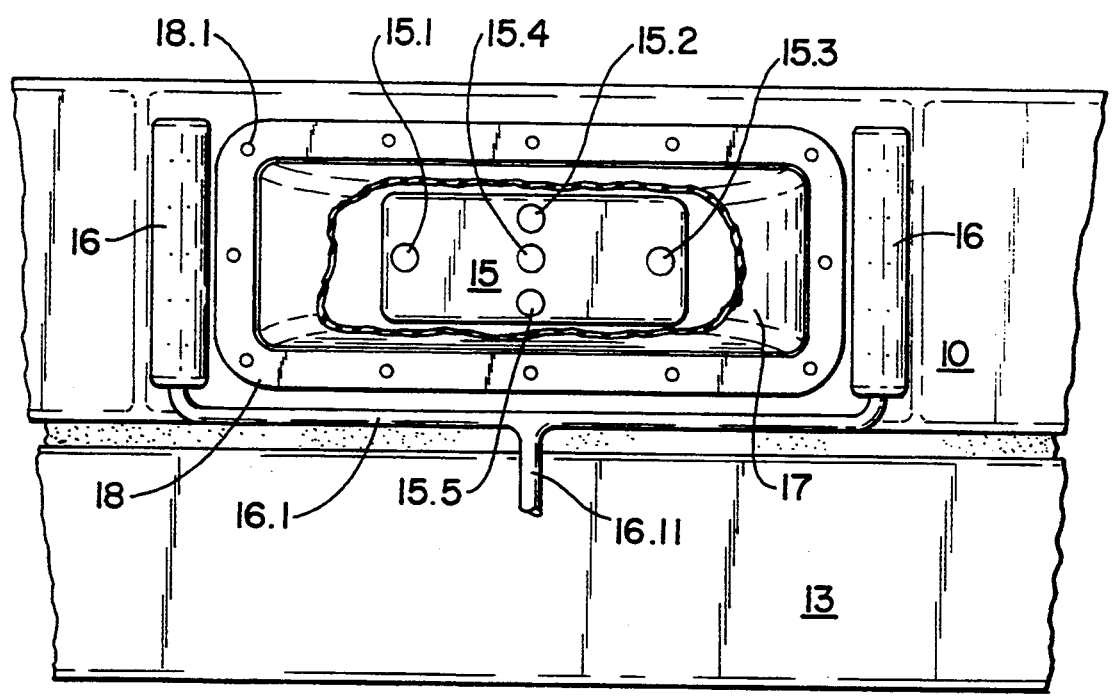
FIG. 3 is a view along line 3—3 in FIG. 2.

With the aid of FIG. 3, it can be seen that the probe transducer assembly 15 may include as five transducers 15.1—15.5, each capable of transceiver operation. The bladder 17 is attached to the bottom of the probe by an attachment ring 18, which is screwed on to the bottom of the probe with fasteners 18.1, an arrangement sandwiching the edge of the bladder between the ring and the probe to provide a fluid tight seal between the bladder and probe. FIG. 3 shows that the wiper 16 may only need to be located on two opposite sides of the bladder with a supply line 16.1 connecting the two wipers to a common supply line 16.2. There are several ways to construct the wipers. They can be constructed of materials similar to a commonly available garden hose soaker (semipermeable to water or with small holes), but wrapped in foam rubber that just contacts the wall without providing much resistance. Alternatively the wiper 16 could be a brush lubricated by occasional drop of fluid. Other possibilities are the use of a miniature roller also wetted with fluid provided under positive pressure. On the other hand, the wiper does not have to necessarily contact the rotor bore tube with a fine set of holes capable of providing a weep or spray of fluid, can be located at a distance from the rotor wall.

The bladder must be thin of course, but a practical constraint is that its thickness should be about 0.25 the wavelength of the ultrasonic sound waves are produced by the transducers. The bladder obviously must be mechanically rugged and flexible, and various plastic polymers and rubbers that have been used for boot heads in other applications, such as spark plugs are constructed suitable material for this application. The fluid that is supplied in the wipers or alternatively that is simply applied to the interior of the wall of the rotor provides a reliable ultrasonic connection between the wall and the bladder.

During an inspection of the rotor with a system embodying the present invention, the rod 12 is extended and retracted within the rotor bore and at the same time rotated, providing longitudinal and radial inspection of the bore. The fluid in line 14 is maintained at a pressure that gives the bladder flexibility to conform to the bore shape. If the pressure is too high, the bladder will not properly conform to that shape. If it is too low, there may be insufficient bladder contact. The pressure may also be controlled to expand the bladder so that it contacts the inner walls when the rod 12 is held in place.

With the benefit of the foregoing discussion, one skilled in the art may be able to make modifications and variations whole or in part to what has been shown and described without departing from the true scope and spirit of the invention.

What is claimed:

1. Apparatus comprising a transducer housing and a transducer in the transducer housing, characterized by;
    first means for longitudinally extending and axially rotating the housing in a bore;
    second means for supplying fluid under controlled pressure to the housing; and
    third means on the housing at a distance from the transducer for resiliently communicating with a bore surface under pressure from the fluid and for transmitting a transducer output to the bore surface.

2. An apparatus according to claim 1, characterized in that the third means comprises a bladder located on a surface of the housing, separated from the transducer by fluid and urged outwardly toward the bore surface by the pressure of fluid in the housing.

3. An apparatus according to claim 1, further characterized by fourth means for providing fluid to a surface of the third means that contacts the bore surface.

4. An apparatus according to claim 3, characterized in that the fourth means comprises means on a perimeter of the third means for providing fluid to the bore surface.

5. An apparatus according to claim 4, characterized in that the fourth means comprises a soaker conduit.

6. An apparatus comprising a transducer housing and a transducer within the housing, characterized by:
    an extension rod attached to the housing for adjustably positioning the housing and containing a passage that communicates with a fluid part in the housing, and adapted to receive fluid under controlled pressure;
    a flexible bladder on one surface of the housing at a distance from a transducer output; and
    a fluid soaker located on an outside surface of the housing along a perimeter of the bladder and containing an inlet for receiving fluid under pressure.

7. A method of testing a rotor bore, comprised by the steps:
    longitudinally and radially locating a transducer contained within a housing along an interior of the bore;
    applying fluid under a controlled pressure to an interior of the housing containing the transducer to expand a flexible surface of the housing against an inner bore surface; and
    transmitting a transducer output from the transducer through the flexible surface to the inner bore surface.

8. The method of claim 7, wherein the step of applying fluid under pressure includes providing fluid under pressure to a soaker member located in proximity to the flexible surface and the inner bore surface.

* * * * *